United States Patent [19]

Jessel, Jr. et al.

[11] Plant 4,622

[45] Jan. 13, 1981

[54] CHRYSANTHEMUM PLANT

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 37,571

[22] Filed: May 9, 1979

[51] Int. Cl.[3] ..... A01H 5/00

[52] U.S. Cl. ..... Plt./74

[58] Field of Search ..... Plt./74

*Primary Examiner*—Robert E. Bagwill

*Assistant Examiner*—James R. Feyrer

*Attorney, Agent, or Firm*—Donald D. Jeffery

[57] ABSTRACT

A chrysanthemum cultivar particularly characterized as to uniqueness by the combined characteristics of flat capitulum form; spooned daisy capitulum type; dark yellow ray floret color; yellow green (immature) to yellow (mature) disc floret color; diameter across face of capitulum ranging from 95 to 110 mm. at maturity; uniform nine week photoperiodic flowering response to short days; medium plant height when grown as a single stem cut spray; and semi-upright branching pattern.

7 Drawing Figures

The present invention comprises a new and distinct cultivar of *Chrysanthemum morifolium,* Ramat., hereinafter referred to by the cultivar name Futura.

Futura is a product of a planned breeding program which had the objective of creating new chrysanthemum cultivars with spooned daisy capitulum type, with yellow ray floret color, with eight or nine week flowering response, and with the ability to produce commercially acceptable quality in year round cut mum programs. Such traits in combination were not present in previously available commercial cultivars.

Futura was originated from a cross made in a controlled breeding program in Barberton, Ohio in 1975. The female parent was Frost, disclosed in U.S. Plant Pat. No. 4,129. The male parent of Futura was Jamboree, disclosed in U.S. Plant Pat. No. 4,156. Both Frost and Jamboree are products of the breeding program of the present inventors.

Futura was discovered and selected as one flowering plant within the progeny of the stated cross by Walter H. Jessel, Jr. and William E. Duffett on Nov. 12, 1976 in a controlled environment in Barberton, Ohio.

The first act of asexual reproduction of Futura was accomplished when vegetative cuttings were taken from the initial selection in January, 1977 in a controlled environment in Barberton, Ohio, by a technician working under formulations established and supervised by Walter H. Jessel, Jr. and William E. Duffett. Continued asexual reproduction by vegetative cuttings for evaluative tests in flowering and stock programs in conjunction with horticultural examination of selected plants initiated Nov. 7, 1977 has demonstrated that the combination of characteristics as herein disclosed for Futura are firmly fixed and are retained through successive generations of asexual reproduction.

Futura has not been observed under all possible environmental conditions. The phenotype may vary significantly with variations in environment such as temperature, light intensity, and day length. The following observations, measurements and comparisons describe plants grown in Barberton, Ohio and Salinas, Calif. under greenhouse conditions which approximate those generally used in commercial practice.

The following traits have been repeatedly observed and are determined to be basic characteristics of Futura which in combination distinguish this chrysanthemum as a new and distinct cultivar:

(1) Flat capitulum form.

(2) Spooned daisy capitulum type.

(3) Dark yellow ray floret color.

(4) Yellow-green (immature) to yellow (mature) disc floret color.

(5) Diameter across face of capitulum ranging from 95 to 110 mm. at maturity.

(6) Uniform nine week photoperiodic flowering response to short days.

(7) Medium plant height (attaining a height of 60 to 65 cm. as a flowered single stem cut spray from a rooted cutting planted to short days from May through November flowerings).

(8) Semi-upright branching pattern.

The accompanying photographic drawings show typical inflorescence and foliage characteristics of Futura.

Sheet 1 is a color photograph of Futura grown as a single stem cut spray. Some difficulty was encountered in obtaining accurate ray floret color representation, with the depicted color being more gold, less yellow, than the actual ray floret color of Futura. The color readings as stated within the disclosure text are, however, correct.

Sheet 2 is a black and white photograph showing three views of the inflorescence of Futura.

Sheet 3 is a black and white photograph showing the foliage of Futura at three stages of growth.

Of the many commercial cultivars known to the present inventors, the most similar in comparison to Futura is Yellow Frost, U.S. Plant Pat. No. 4,220. Reference is made to attached Chart A which compares certain characteristics of Futura to those same characteristics of Yellow Frost.

In comparison to Yellow Frost, Futura has darker ray floret color and larger diameter across face of capitulum. The capitulum form, capitulum type, plant height, and flowering response period of Futura are similar to those same characteristics of Yellow Frost.

In the following description color references are made to A Limit Color Cascade by the Munsell Company, 1972 edition. The color values were determined between 1:00 and 1:30 p.m. on Nov. 7, 1978 under 90 foot-candle light intensity at Salinas, Calif.

Classification

*Botanical.*—*Chrysanthemum morifolium,* Ramat., cv Futura.

*Commercial.*—Natural spray for cut flower programs.

I. Inflorescence

A. *Capitulum.*—(See sheets 1 and 2 of drawings). Form: Flat. Type: Spooned daisy. Diameter across face: 95 to 110 mm.

B. *Corolla of ray florets.*—Shape: Tubular, with flare at tip. Persistence: Resists shatter. Color (abaxial): 26-3 to 26-4 inside petal tip. Color (adaxial): 26-3 to 26-4.

C. *Corolla of disc florets.*—Color (abaxial): 22-10 (immature) to 26-8 (mature).

D. *Reproductive organs.*—Androecium: Present disc florets only; scant to numerous; scant pollen. Gynoecium: Present both ray and disc florets.

II. Plant

A. *General appearance.*—Height: Medium, ranging from 60 to 65 cm. as a flowered single stem cut spray from a rooted cutting planted to short days for May through November flowerings. Branching pattern: Semi-upright.

B. *Foliage.*—(See sheets 1 and 3). Color (abaxial): Approximately 21-15. Color (adaxial): Approximately 21-14. Shape: Deeply lobed, moderately serrated.

CHART A

COMPARISON OF FUTURA AND YELLOW FROST

| CULTIVAR | RAY FLORET COLOR | CAPITULUM FORM AND TYPE | DIAMETER ACROSS FACE OF CAPITULUM |
|---|---|---|---|
| Futura | Dark Yellow | Flat Spooned daisy | 95 to 110 mm. |
| Yellow Frost | Medium Yellow | Flat spooned daisy | 80 to 95 mm. |

| CULTIVAR | PLANT HEIGHT | FLOWERING RESPONSE PERIOD |
|---|---|---|
| Futura | Medium, 60 to 65 cm. | 9 week |
| Yellow Frost | Medium, 60 to 65 cm. | 9 week |

COMPARISONS MADE OF PLANTS GROWN AS SINGLE STEM CUT SPRAYS IN BARBERTON, OHIO AND IN SALINAS, CALIFORNIA.

We claim:

1. A new and distinct cultivar of *Chrysanthemum morifolium,* Ramat., plant known by the cultivar name Futura as described and illustrated, and particularly characterized as to uniqueness by the combined characteristics of flat capitulum form; spooned daisy capitulum type; dark yellow ray floret color; yellow-green disc floret color; diameter across face of capitulum ranging from 95 to 110 mm. at maturity; uniform nine week photoperiodic flowering response to short days; medium plant height when grown as a single stem cut spray; and semi-upright branching pattern.

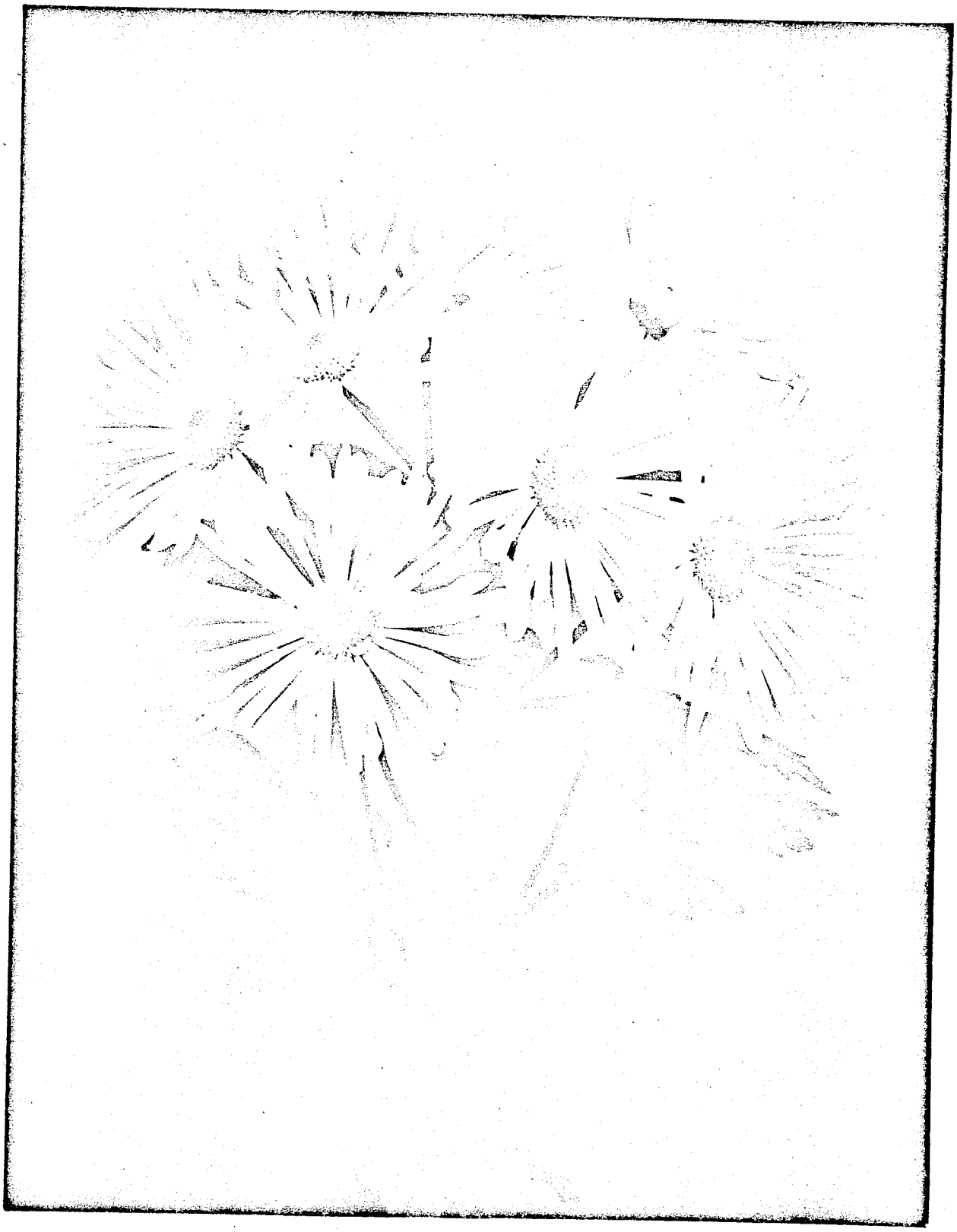

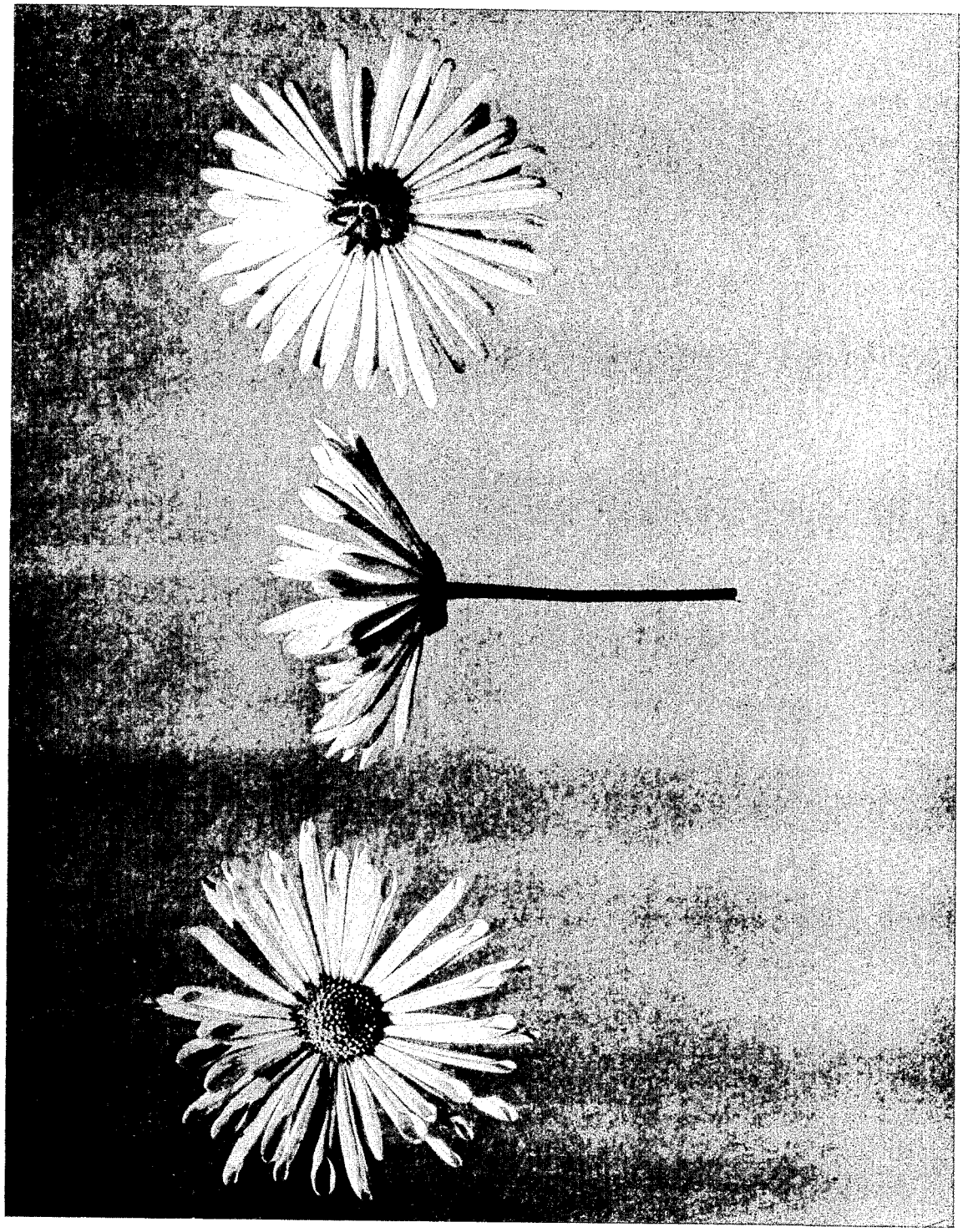

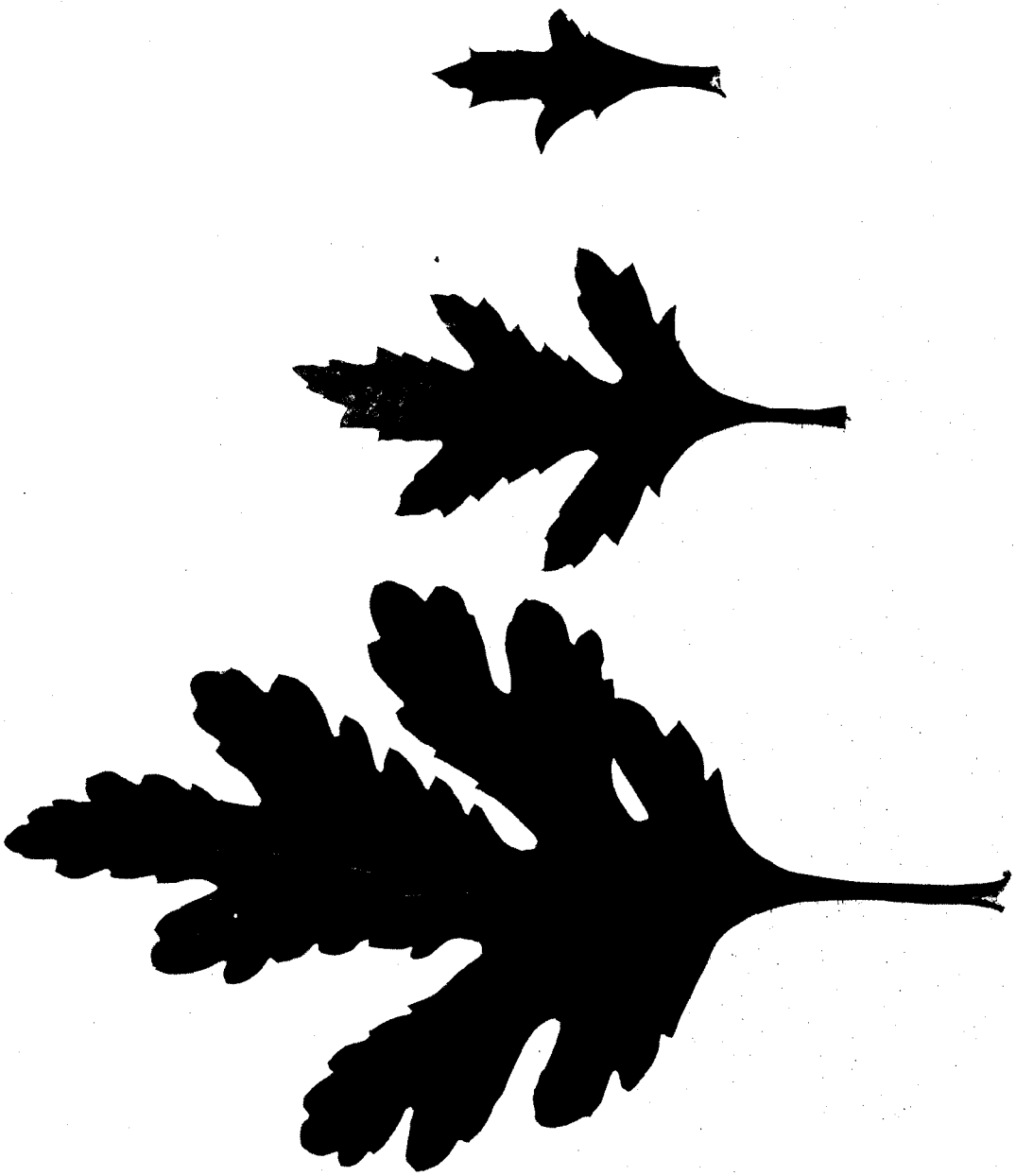

* * * * *